US008916180B2

(12) United States Patent
Scimeca et al.

(10) Patent No.: US 8,916,180 B2
(45) Date of Patent: *Dec. 23, 2014

(54) COSMETIC TREATMENT SYSTEM AND METHODS

(71) Applicant: Access Business Group International LLC, Ada, MI (US)

(72) Inventors: John V. Scimeca, Kentwood, MI (US); Amy C. Zimmerman, Grand Rapids, MI (US); Mark F. Mettler, Spring Lake, MI (US); Akiko Kudo, Tokyo (JP); Yoko Kawasaki, Tokyo (JP)

(73) Assignee: Access Business Group International LLC, Ada, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/184,244

(22) Filed: Feb. 19, 2014

(65) Prior Publication Data

US 2014/0186433 A1    Jul. 3, 2014

Related U.S. Application Data

(60) Division of application No. 12/839,202, filed on Jul. 19, 2010, now Pat. No. 8,697,099, which is a continuation of application No. 11/784,159, filed on Apr. 5, 2007, now Pat. No. 7,758,878, which is a continuation of application No. PCT/US2005/012033, filed on Apr. 12, 2005, which is a continuation-in-part of application No. PCT/US2004/033419, filed on Oct. 7, 2004.

(60) Provisional application No. 60/510,307, filed on Oct. 10, 2003.

(51) Int. Cl.
| A61K 8/00 | (2006.01) |
| A61K 38/43 | (2006.01) |
| A61K 36/53 | (2006.01) |
| A61K 36/47 | (2006.01) |
| A61K 36/28 | (2006.01) |
| A61K 8/97 | (2006.01) |

(52) U.S. Cl.
USPC .......... 424/401; 424/94.1; 424/725; 424/778; 424/737; 424/774; 424/736; 424/764; 424/776

(58) Field of Classification Search
CPC ........... A61Q 19/08; A61K 8/66; A61K 8/97; A61K 36/53; A61K 36/25; A61K 36/28; A61K 36/9062
See application file for complete search history.

(56) References Cited

U.S. PATENT DOCUMENTS

| 5,296,231 A | 3/1994 | Yarosh |
| 6,063,398 A | 5/2000 | Gueret |
| 6,096,334 A | 8/2000 | Rolf et al. |
| 6,120,792 A | 9/2000 | Juni |
| 6,267,971 B1 | 7/2001 | Breton et al. |
| 6,368,594 B1 | 4/2002 | Doetsch et al. |
| 6,479,533 B1 | 11/2002 | Yarosh |
| 6,495,158 B1 | 12/2002 | Buseman et al. |
| 6,589,514 B2 | 7/2003 | Jensen et al. |
| 6,623,751 B2 | 9/2003 | Gueret |
| 6,660,283 B2 | 12/2003 | Breton et al. |
| 2002/0048594 A1 | 4/2002 | Breton et al. |
| 2002/0086043 A1 | 7/2002 | Gueret |
| 2003/0152610 A1 | 8/2003 | Rolf et al. |
| 2003/0175328 A1 | 9/2003 | Shefer et al. |
| 2003/0223982 A1 | 12/2003 | Schlotmann et al. |
| 2004/0057917 A1 | 3/2004 | Wolf et al. |
| 2006/0002884 A1 | 1/2006 | Golz-Berner et al. |

FOREIGN PATENT DOCUMENTS

| EP | 0 707 844 A2 | 4/1996 |
| EP | 0 976 396 | 2/2000 |
| EP | 1 410 790 | 5/2004 |
| FR | 2 746 316 | 9/1997 |
| JP | H10-45559 | 2/1998 |
| JP | 2001019628 | 1/2001 |
| WO | WO 02/49593 | 6/2002 |
| WO | WO 2004/004673 | 1/2004 |
| WO | WO 2005/034891 | 4/2005 |
| WO | WO 2006/041526 | 4/2006 |

OTHER PUBLICATIONS

Yadav, P. et al., Abstract: "A Diarylheptanoid from Lesser Galangal (*Alpinia officinarum*) Inhibits Proinflammatory Mediators via Inhibition of Mitogen-Activated Protein Kinase, p. 44/42, and Transcription Factor Nulcear Factor—$_kB$", *The Journal of Pharmacology and Experimental Therapeutics Fast Forward*, vol. 305, No. 3, pp. 925, Mar. 6, 2003.

Lee, K et al., Abstract: "Inhibitory Effects of 150 Plant Extracts on Elastase Activity, and Their Anti-Inflammatory Effects", *International Journal of Cosmetic Science*, Apr. 1999;21(2):doi: 10.1046/j. 1467-2494.1999.181638.x (http://www.ncbi.nlm.nih.gov/pubmed/18505532).

PCT/US2004/033419 International Search Report dated Apr. 13, 2005 (3 pages).

PCT/US2005/012033 International Search Report dated Jul. 5, 2005 (3 pages).

*Primary Examiner* — Maria Marvich
(74) *Attorney, Agent, or Firm* — Brinks Gilson & Lione; G. Peter Nichols

(57) ABSTRACT

A cosmetic treatment system is provided having ingredients that may prevent signs of aging, improve the aesthetic appearance of skin, and promote recovery from environmental stresses. The composition includes natural ingredients, including at least one ingredient or extract from rosemary; at least one ingredient or extract from *Centella, Echinacea, Alpinia* or mixtures thereof; a DNA repair enzyme; and at least one pharmaceutically or cosmetically acceptable vehicle. The treatment system may further include a patch for applying the cosmetic ingredients and/or a packaging system for holding the components of the cosmetic treatment system.

9 Claims, 9 Drawing Sheets

FIGURE 7a
FIGURE 7b
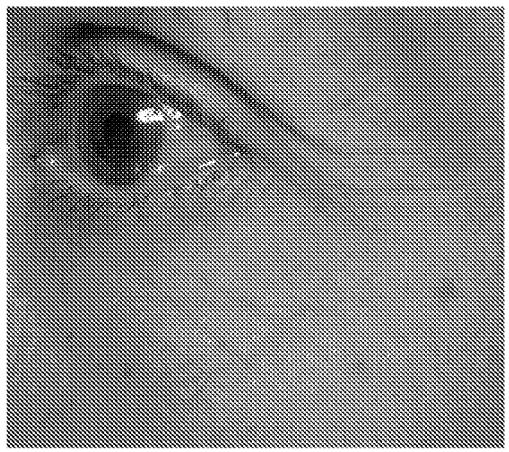
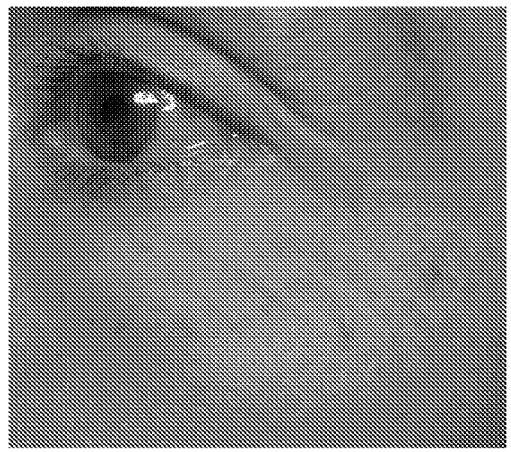
FIGURE 8a
FIGURE 8b
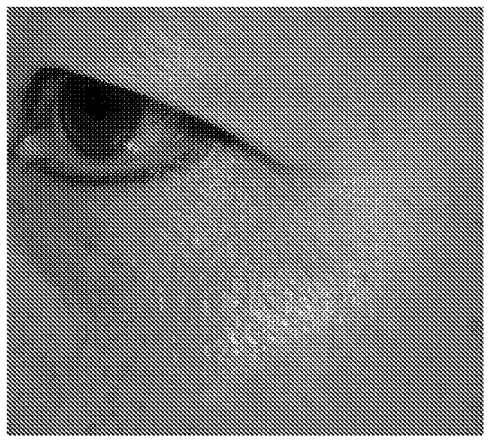
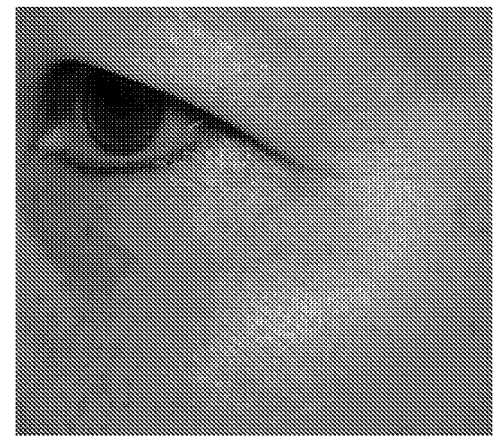

COSMETIC TREATMENT SYSTEM AND METHODS

This application is a divisional of U.S. application Ser. No. 12/839,202 filed Jul. 19, 2010, now U.S. Pat. No. 8,697,099, which is a continuation of U.S. application Ser. No. 11/784,159 filed on Apr. 5, 2007 which issued on Jul. 20, 2010 as U.S. Pat. No. 7,758,878, which is a continuation of PCT International Application No. PCT/US2005/0012033 filed Apr. 12, 2005, which was published in English as WO 2006/041526 on Apr. 20, 2006, and which is a continuation-in-part of PCT International Application No. PCT/US04/033419, filed Oct. 7, 2004, which was published in English as WO2005/034891 on Apr. 21, 2005, which claims priority to U.S. Ser. No. 60/510,307 filed Oct. 10, 2003, the entire contents of which are incorporated herein by reference.

BACKGROUND

The present invention relates to topical cosmetic compositions that incorporate materials to stimulate DNA repair mechanisms to repair skin cells. The disclosed compositions and methods may prevent, reduce, or reverse signs of premature aging, and/or improve the aesthetic appearance of skin. Use of the compositions may stimulate the skin's natural ability to recover from environmental stresses and prevent signs of premature aging. The compositions include natural active ingredients derived from natural plant materials, as well as enzymes for repairing DNA damage.

The skin is made up of two major layers. The stratum corneum, or epidermis, is the top or outer layer of the skin. The primary function of the stratum corneum is to provide a protective covering and retard evaporative water loss from the aqueous interior. This is commonly referred to as the barrier function. The stratum corneum protects against mechanical insults, the ingress of foreign chemicals and assaults by microorganisms. It also provides the first defense against ultraviolet light, screening out more than 80% of incident ultraviolet B irradiation.

The dermis lies under the epidermis and makes up 90 percent of the skin's thickness. The dermis contains a dense meshwork of collagen and elastin, providing strength and elasticity to the skin. Fibroblasts constitute the main cell type present in the dermis. Fibroblasts are responsible for synthesis and secretion of dermal matrix components, including collagen, elastin, and glycosaminoglycans (such as hyaluronic acid). Whereas collagen provides strength to the skin and elastin its elasticity, glycosaminoglycans serve to keep the skin moist and plump.

To stay healthy, the skin must cope with changing environmental conditions, while simultaneously repairing damage. Environmental factors play a chief role in aging, wrinkles, skin discolorations and degenerative skin conditions. Exposure to sunlight and UV radiation are major factors resulting in skin damage, accounting for 90% of the symptoms of premature aging. Importantly, exposure to oxygen, sunlight, and other environmental or lifestyle stresses induces the formation of free-radicals. Free radicals can cause wrinkles by activating metalloproteases, such as collagenases, that are responsible for breaking down the skin's connective tissues (collagen and elastin). The result is premature aging. Free-radical damage can also cause a reduction in the thickness of the dermal layer. This can cause the skin to slacken. The slackening of the skin is the first and most visible sign of aging and a cause of wrinkles and lines.

Sunlight also can cause the accumulation of abnormal elastin by triggering the overproduction of metalloproteinases. Normally, metalloproteinases remodel sun-injured skin by manufacturing and reforming collagen. Repeatedly subjecting the skin to this imperfect rebuilding process may lead to formation of wrinkles or solar scars. Exposure to the sun also can rob the skin of essential moisture and create a stressed barrier that does not function properly. As moisture loss and irritation increase, the skin becomes sensitive, scaly, and dry.

Although oxygen and sunlight constitute the principal sources of free-radical damage, other contributors include cigarette smoke, environmental toxins, herbicides, pesticides, weather, diet, stress, sleep deprivation, excessive alcohol consumption, and pollution.

UV radiation from the sun may also damage DNA and may bring about several detrimental effects including cell death, mutation and neoplastic transformation. Studies indicate that some of these deleterious effects are due to the formation of two major classes of bipyrimidine DNA photoproducts, cyclobutane pyrimidine dimers (CPDs) and (6-4) photoproducts (6-4 PPs). Organisms have evolved several different pathways for removing CPDs and 6-4 PPs from cellular DNA. These pathways include various excision repair pathways which can be highly specific or nonspecific for CPDs and 6-4 PPs.

In view of the many detrimental effects impacting the skin, there is a demand for cosmetic compositions and cosmetic methods for improving the appearance and condition of skin. Consumers seek "anti-aging" cosmetic products that treat or delay the visible signs of actual aging and weathered skin, such as wrinkles, lines, sagging, hyperpigmentation and age spots. Consumers also seek other benefits from cosmetic products in addition to anti-aging benefits. For example, the concept of "sensitive skin" has raised the demand for cosmetic products that improve the appearance and condition of sensitive, dry and/or flaky skin, and that soothe red, and/or irritated skin. Consumers also desire cosmetic products that treat spots, pimples, blemishes, and the like, or that reduce the risk of skin cancer.

In spite of the various anti-aging cosmetic products on the market for the treatment of skin, there remains a need for effective topically applied cosmetic compositions that provide anti-aging or rejuvenating benefits to the skin, hair and/or nails using natural ingredients as active components. Unnatural, chemically-synthesized products may be perceived as being environmentally or personally unsafe. In contrast, natural products are perceived as pure, mild, and superior to chemically synthesized products. Natural based products extracted from plants or herbs are believed to contain antioxidant/free-radical scavenging agents that can neutralize the effects of free-radical damage. Additionally, they can contain agents that stimulate the synthesis and restoration of damaged connective tissue structures in the dermis and barrier function in the epidermis.

However, delivering a cosmetic benefit from "natural" sources, such as plants or herbs, is not trivial. Deriving a real benefit from such sources requires identification of specific plant/herbal extracts or ingredients, their minimum active concentrations, and their additive or synergistic activities in combination with other ingredients to impart anti-aging and/or skin improvement benefits.

The present compositions further address the frequent irritation problems associated with exfoliating agents such as retinoids (e.g., tretinoin, retinol and retinal), carboxylic acids including α-hydroxy acids (e.g., lactic acid, glycolic acid), β-hydroxy acids (e.g., salicylic acid), α-keto acids, acetic acid and trichloroacetic acid, 1-pyrrolidone-5-carboxylic acid, capryloyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others. Exfoliants and other ingredients may also increase the skin's sensitivity to environmental conditions such as sunlight, wind, cold temperature and dry air, or may exacerbate the irritation attributable to a pre-existing skin disease.

The present invention therefore provides cosmetic compositions for topical use that have anti-aging, anti-oxidant, anti-irritant, anti-inflammatory, and/or aesthetic improvement properties. The cosmetic compositions of the present invention may reduce irritation problems that may be encountered with conventional exfoliating agents.

BRIEF SUMMARY

In one embodiment, the present invention provides a skin treatment system including a topical composition having a *Rosmarinus officinalis* plant ingredient or extract; at least one plant ingredient or extract from *Centella, Echinacea, Alpinia*, or mixtures thereof; a DNA repair enzyme; and a pharmaceutically or cosmetically acceptable vehicle.

In a particular embodiment, the topical composition may include a *Rosmarinus officinalis* plant ingredient or extract; a *Centella asiatica* plant ingredient or extract; an *Echinacea angustifolia* plant ingredient or extract; an *Alpinia speciosa* plant ingredient or extract; and a liposome-encapsulated *Micrococcus luteus* N-glycosylase/AP lyase enzyme.

In another embodiment, the topical composition may include a *Rosmarinus officinalis* plant ingredient or extract; an *Alpinia speciosa* plant ingredient or extract; and a liposome-encapsulated *Micrococcus luteus* N-glycosylase/AP lyase enzyme.

The composition may include other cosmetically active plant or botanical ingredients present in, or in the form of, castor seed oil, Licorice root extract, seaweed extract, lemon extract, cucumber extract, sunflower seed extract, hydrolyzed oats, oat (*Avena sativa*) kernel extract, evening primrose seed extract (e.g., Lunawhite B), hydrolyzed soy protein, yeast extract (e.g., Toniskin), *Lentinus enodes* extract (e.g., Fermiskin), *Perilla ocymoides* leaf extract (e.g., Shiso extract), *Perilla frutescens* leaf extract, *Nymphaea alba* flower extract (e.g., Nympheline), silk proteins and/or combinations or derivatives thereof, and may further include a variety of vitamins, minerals, anti-oxidants, amino acids and/or other cosmetically active agents. A suitable source for the plant or botanical ingredients is Barnet Products Corp., Englewood Cliffs, N.J.

The skin treatment system may further include a patch to aid in delivery of the topical composition and a packaging system for holding components of the skin treatment system.

In a particular embodiment, a skin treatment system is provided using a patch impregnated with a topical composition of the present invention formulated for treatment of the area around the eyes.

The active ingredients may be obtained from seeds, needles, leaves, roots, bark, cones, stems, rhizomes, callus cells, protoplasts, organs and organ systems, or meristems. The active ingredients may be incorporated in the present compositions in a variety of forms. Such forms include a pure or semi-pure component, a solid or liquid (e.g. oil) extract or derivative, or a solid plant matter. The plant matter may also be incorporated in various subforms, including whole, minced, ground or crushed.

The present invention may also provide a method of improving the aesthetic appearance of skin, in which a composition of the present invention is topically applied to skin in a cosmetically effective amount. In a further aspect, the present invention provides a method to stimulate the skin's natural ability to recover from environmental stresses and/or prevent or reverse the signs of aging, in which a composition of the present invention is topically applied to skin areas typically exposed to UV rays or other environmental stresses.

The cosmetic composition of the present invention may be applied to the skin at a frequency of at least once a day. When the cosmetic composition is applied to the skin once a day, it is desirable to apply the composition in the evening so that further environmental insults to the skin are reduced. The cosmetic composition may be applied to skin for a period of time effective to provide anti-aging benefits and/or an improved aesthetic appearance. In one embodiment, the composition is applied at least once daily, for a period of fourteen days or longer.

All percentages recited in the present specification and appended claims are expressed in terms of weight/weight, unless specifically stated otherwise.

BRIEF DESCRIPTION OF THE DRAWINGS

FIG. 7*a* is a photograph of a portion of a subject's face before application of the composition of the present invention. FIG. 7*b* is a photograph of a portion of the subject's face after daily application of a composition of the present invention over a period of fourteen days.

FIG. 8*a* is a photograph of a portion of another subject's face before application of the composition of the present invention. FIG. 8*b* is a photograph of a portion of the subject's face after daily application of a composition of the present invention over a period of fourteen days.

DETAILED DESCRIPTION

Figure 1A:
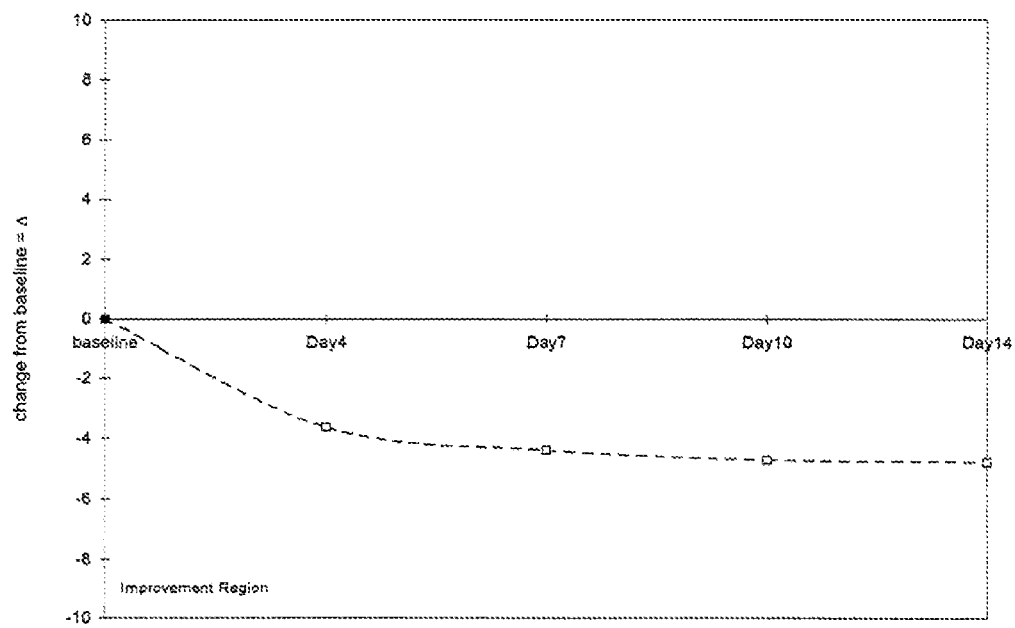
FIG. 1*a* is a graph depicting a reduction of fine skin lines when a representative composition of the present invention was topically applied to the skin over a 14 day period.

In order to provide a clear and consistent understanding of the specification and claims, the following definitions are provided.

"Improving at least one sign of aging" and "improving a sign of aging" are used interchangeably herein to designate preventing, arresting, reversing, ameliorating, diminishing, and/or reducing a sign of aging. Representative signs of aging include, but are not limited to, lines, fine lines, wrinkles, crow's feet, dark eye circles, blemishes, age spots, stretch marks, or combinations thereof.

"Improving the appearance of skin" and "improving the aesthetic appearance of skin" are used interchangeably herein to designate an aesthetic improvement in the appearance of skin. Representative improvements may include, but are not limited to, favorable characteristics and/or properties related skin thickness, elasticity, resiliency, moisturization, smoothness, tone, texture, radiance, luster, brightness, clarity, contour, firmness, tautness, suppleness, softness, sensitivity, pore size, or combinations thereof. These terms may also be used to designate an improvement in an adverse skin condition. Representative adverse conditions affecting by, resulting in or resulting from such an adverse skin condition include, but are not limited to, psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, tactile roughness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The present invention provides a cosmetic treatment system having a topical composition including, a *Rosmarinus officinalis* plant ingredient or plant extract; at least one plant ingredient or plant extract from *Centella, Echinacea, Alpinia*, or mixtures thereof; a DNA repair enzyme; and a pharmaceutically or cosmetically acceptable vehicle.

Application of the topical composition of the present invention may improve the aesthetic appearance of the skin, and may rejuvenate or enhance the skin. The compositions of the present invention may also provide a variety of anti-aging and skin texture benefits. It is believed that the combination of ingredients used in the present invention provides significant anti-aging and skin texture benefits relative to the individual ingredients therein. Topical application of the ingredient combinations may produce benefits that are additive or synergistic relative to application of the individual ingredients therein.

The present invention may provide benefits to skin relating to anti-aging and improved aesthetic appearance. Accordingly, the present invention provides topical compositions and methods for their use in treating skin to prevent, arrest, reverse, ameliorate, diminish, reduce or improve signs of aging, including, or associated with, chronological aging, hormonal aging, and/or photoaging. The signs of aging may include, but are not limited to, skin fragility; loss of collagen and/or elastin; estrogen imbalance in skin; skin atrophy; appearance and/or depth of lines and/or wrinkles, including fine lines; skin discoloration, including dark eye circles; crow's feet; skin sagging; skin fatigue and/or stress, e.g., skin breakout due to environmental stress, such as pollution and/or temperature changes; skin dryness, fine lines due to skin dryness, skin roughness; skin flakiness; cellular aging; loss of skin tone, elasticity, clarity, luminosity, and/or luster; loss of skin firmness; poor skin texture; loss of skin elasticity and/or resiliency; thin skin, and inflammation.

The benefits and improvements to the aesthetic appearance of skin can be manifested in any of the following: reduction in pore size, fine lines, wrinkles, tactile roughness, and inflammation; improvement in skin tone, radiance, clarity and/or tautness; promotion of anti-oxidant activity; improvement in skin firmness, plumpness, suppleness, and/or softness; improvement in procollagen and/or collagen production; improvement in skin texture and/or promotion of retexturization; improvement in skin barrier repair and/or function; improvement in appearance of skin contours; restoration of skin luster, clarity, and/or brightness; replenishment of essential nutrients and/or constituents in the skin decreased by aging and/or menopause; improvement in communication among skin cells; increase in cell proliferation and/or multiplication; increase in skin cell metabolism decreased by aging and/or menopause; improvement in skin moisturization; promotion and/or acceleration of cell turnover; enhancement of skin thickness; increase in skin elasticity and/or resiliency; and enhancement of exfoliation, with or without the use of alpha or beta hydroxy acids, keto acids or other exfoliants.

Other benefits may include an increase in skin smoothness and/or softness, an increase in the perception of skin condition, an increase in skin moisture, a reduction in skin stress and fine lines, an increase in brightness, improved skin texture and skin firmness.

In one embodiment of the present invention, the topical composition includes a plant ingredient or plant extract from *Rosmarinus officinalis* (Rosemary extract); at least one plant ingredient or plant extract from *Centella, Echinacea, Alpinia*, or mixtures thereof; a DNA repair enzyme; and a pharmaceutically or cosmetically acceptable vehicle.

Compositions of the present invention include an ingredient or extract from *Rosmarinus officinalis* (e.g., Rosemary extract). Ingredients from Rosemary are believed to have anti-aging, anti-cancer, anti-inflammatory, anti-microbial properties and/or low toxicity. Active ingredients in Rosemary are believed to include, but are not limited to, ursolic acid, carnosol, carnosic acid, rosmarinic acid and oleanolic acid. Active ingredients in *Rosmarinus officinalis* are believed to restore the skin's collagen bundle structures and elasticity, and/or to prevent or improve the appearance of lines, fine lines, wrinkles and/or age spots. Part of this appears to be attributed to ursolic acid and carnosic acid, which are believed to downregulate the enzymatic activity of metalloproteinase enzymes responsible for breakdown of collagen and elastin. Rosemary extract ingredients believed to function as anti-oxidants, include, but are not limited to carnasol, carnosic acid, rosmarinic acid and ursolic acid. Ursolic acid is believed to be a potent anti-inflammatory agent, to form oil-resistant barriers on the skin, and to improve the skin barrier function. Moreover, ursolic acid and oleanolic acid have also been shown to inhibit tumor promotion. Consequently, the use of these agents may provide the added benefit of protecting against the onset or promotion of skin cancer.

Other plant or botanical sources containing ursolic acid that may be used in the present invention include, but are not limited to, holy basil (tulsi; *Ocimum sanctum*), bilberry (*Vaccinum myrtillus*), devil's claw (*Harpagophytum procumbens*), elder flowers (*Sambucus nigra*), peppermint leaves (*Mentha piperita*), periwinkle (*Vinca minor*), lavender (*Lavendula augustifolia*), oregeno (*Origanum vulgare*), thyme (*Thymus vulgaris*), hawthorn (*Crataegu laevigata*), cherry laurel leaves (*Prunus laurocerasus*), and ground ivy (*Glechoma hederacea*).

The present invention may also include a plant ingredient or plant extract from *Centella*, *Echinacea*, *Alpinia*, or mixtures thereof. The ingredient or extract may be from any species members of these genus groups.

In a particular embodiment, the topical composition may include a *Rosmarinus officinalis* plant ingredient or extract; a *Centella asiatica* plant ingredient or extract; an *Echinacea angustifolia* plant ingredient or extract; an *Alpinia speciosa* plant ingredient or extract; and a liposome-encapsulated *Micrococcus luteus* N-glycosylase/AP lyase enzyme.

In another embodiment, the topical composition may include a *Rosmarinus officinalis* plant ingredient or extract; an *Alpinia speciosa* plant ingredient or extract; and a liposome-encapsulated *Micrococcus luteus* N-glycosylase/AP lyase enzyme.

*Centella* or *Centella asiatica* belongs to the Hydrocotyl genus and also is known as Gotu Kola or Indian Pennywort. *Centella asiatica* is believed to contain several active ingredients, including three triterpenes, asiatic acid, madecassic acid and asiaticoside. These ingredients are believed to be useful anti-wrinkle/anti-aging ingredients on account of several recognized properties. Specifically, *Centella* agents are believed to act upon connective tissue, where they are thought to increase collagen and glycosaminoglycan synthesis, increase connective tissue remodeling and elasticity, modulate fibroblast activity and/or metabolism, and act as an anti-inflammatory agent. Additionally, the *Centella* triterpenes have been found to dose-dependently inhibit free radical-induced collagen degradation. Of the three triterpenes, asiaticoside has been found to induce collagen synthesis and to elevate enzymatic and non-enzymatic anti-oxidant activities of vitamin E, vitamin C, superoxide dismutatse, catalase, and glutathione peroxidase. *Centella* also is believed to have anti-inflammatory properties and has been used traditionally for treating eczema and for minor itching and insect bites.

*Echinacea* or coneflower is believed to exist in at least three varieties, *Echinacea purpurea*, *Echinacea angustifolia*, and *Echinaceea pallida*. Total *Echinacea* extracts and echinoside, a caffeoyl derivative present therein, provide protective effects on skin connective tissue and are thought to enhance wound healing. Ingredients in *Echinacea* also are believed to possess anti-bacterial and anti-inflammatory activity and to reduce redness in skin or relieve conditions, such as eczema, insect bites and psoriasis.

*Alpinia* is a rhizomatous herb. Representative *Alpinia* members include, but are not limited to, *Alpinia galanga*, *Alpinia katsumadai*, *Alpinia officinalis*, *Alpinia oxyphylla*, *Alpinia purpurata*, *Alpinia speciosa*, and *Alpinia zerumbet*. *Alpinia* species are believed to promote collagen synthesis and cell growth and to inhibit activity of the collagenase and/or elastase enzymes, which breaks down collagen and elastin in process regulated by the NF-kB pathway. Accordingly, a diarylheptanoid from *Alpinia officinarum* was recently shown to inhibit proinflammatory mediators via inhibition of mitogen activated protein kinase, p44/42 and transcription factor NF-kB (J. Pharmacol. Exp. Ther., 305: 925-931; see also Intl. J. Cosmetic Science, 21(2):71, April 1999). Advantageously, *Alpinia* extracts have been also found to inhibit tumor progression. Consequently, use of *Alpinia* ingredients or extracts may protect against skin cancer. Other compositions of the present invention may include *Alpinia speciosa*.

In a particularly preferred embodiment, the present invention provides a cosmetic treatment system utilizing a topical composition suitably formulated for treatment of the area around the eyes. While not wishing to be bound by theory, it is believed treatment of the eye area can be improved when using a patch impregnated with a composition containing *Rosmarinus officinalis* plant ingredient or extract; an *Alpinia speciosa* plant ingredient or extract; at least one DNA repair enzyme, and one or more additional ingredients including, *Avena sativa* (oat) kernel extract, evening primrose seed extract, L-ergothioneine, hydrolyzed soy protein, yeast extract, *Lentinus enodes* extract, *Nymphaea alba* flower extract, and/or *Perilla frutescens* leaf extract. The additional ingredients are believed to have efficacious properties associated with improving the appearance of fine lines, brightening skin, and/or improving firmness (evening primrose seed extract, L-ergothioneine, hydrolyzed soy protein, yeast extract, *Lentinus* enodes extract); or soothing, smoothing, and/or moisturizing skin (*Avena sativa* (oat) kernel extract, *Perilla frutescens* leaf extract).

The plant ingredients or plant extracts for use in the present invention are generally present in a collective amount ranging from about 0.0001% to 5% by weight of the total composition, desirably from about 0.001 wt % to about wt 0.5%, more desirably from about 0.01 wt % to about 0.1 wt %.

Rosemary extract, or ingredients thereof, may be present in an amount from about 0.001% to about 10% by weight of the composition. Desirably, the Rosemary ingredient or extract is present in an amount from about 0.05 wt % to about 5 wt %, more desirably from 0.01 wt % to about 1 wt %, and still more desirably from about 0.01 wt % to about 0.05 wt %, of the total weight of the composition.

The present invention may include a plant ingredient or plant extract from *Centella* or *Alpinia* (or mixtures thereof), where the at least one plant ingredient or plant extract is present in the composition, individually or collectively, in an amount ranging from about 0.001% to about 10% by weight of the total composition, desirably from about 0.005 wt % to about 2 wt %, more desirably from about 0.02 wt % to about 0.08 wt %. Alternatively, or in addition, the present invention may also include an ingredient or extract from either of the *Echinacea* species, where the ingredient or extract is present in the composition, individually or collectively, in an amount ranging from about 0.0001% to about 1% by weight of the total composition, desirably from about 0.001 wt % to about 0.1 wt %, more desirably from about 0.0005 wt % to about 0.02 wt %.

Each of the ingredients selected from the list including *Avena sativa* (oat) kernel extract, evening primrose seed extract, L-ergothioneine, hydrolyzed soy protein, yeast extract, *Lentinus enodes* extract, *Nymphaea alba* flower extract, and *Perilla frutescens* leaf extract may be applied in an amount ranging from about 0.001 to about 10% by weight of the total composition, desirably from about 0.01 to about 5%, and more desirably from about 0.1 to about 2.5% by weight of the total composition.

The plant ingredients of the present invention may be provided separately from a plant extract or they may be included with a plant extract present in a mixture. For example, *Rosmarinus officinalis* leaf extract with lecithin and water is available as MEROSPHERES from Applied Genetics, Inc. Dermatics, Freeport, N.Y. *Alpinia speciosa* leaf extract in water and butylene glycol is available as ALPINIA LEAF EXTRACT BG from Maruzen Pharmaceuticals Co., Ltd., Hiroshima, Japan. A combination of *Centella asiatica* extract, *Echinacea angustifolia* extract, and *Rosmarinus officinalis* leaf extract may be available in ethoxydiglycol or in dipropylene glycol and SD-alcohol is available as ACTIFIRM ULTRA or ACTIFIRM ULTRA DiPG, respectively, from Active Organics, Lewisville, Tex. Desired embodiments of the present invention may include at least one plant ingredient or plant extract from at least two, or more desirably three members of the group including, *Centella asiatica, Echinacea angustifolia,* and *Alpinia speciosa*.

DNA repair enzymes for use in the present invention may include enzymes involved in either the base excision repair (BER), the nucleotide excision repair (NER) pathway, or alternate excision repair pathways as described in e.g., U.S. Pat. No. 6,368,594. These pathways are mediated by separate sets of proteins capable of carrying out DNA incision, lesion removal, gap-filling, and ligation reactions.

The NER pathway constitutes a widely distributed, lesion non-specific repair pathway orchestrating DNA damage removal via a dual incision reaction upstream and downstream from the damage site resulting in release of an oligonucleotide containing the damage. Following removal of the damaged DNA, the resulting gap is filled and the DNA ends are ligated together.

The BER pathway is the primary defense against all major forms of DNA base damage. This pathway is responsible for detecting and removing a variety of specific, individual base lesions within a large pool of undamaged DNA. BER pathways typically involve the activity of N-glycosylase/AP lyase enzymes specific for CPDs. The N-glycosylase/AP lyase enzymes first cleave the N-glycosidic bond of a CPD 5' pyrimidine and then cleave the phosphodiester backbone at an abasic site via a β-lyase mechanism.

Suitable DNA repair enzymes for use in the present invention have N-glycosylase/AP lyase activities capable of recognizing, excising and repairing damaged DNA, such as CPDs and (6-4) photoproducts. The activity of these enzymes can be light-dependent (e.g., photolyases) or light-independent. Exemplary DNA repair enzymes in this group include, but are not limited to, bacteriophage T4 pyrimidine dimer-specific endonuclease (denV endonuclease), *Micrococcus luteus* N-glycosylase/AP lyase, *Saccharomyces cerevisiae* N-glycosylase/apurinic-apyrimidinic lyase, *Schizosaccharomyces pombe* UV damage endonuclease (UVDE), Chlorella virus isolate PBCV-1 pyrimidine dimer-specific glycosylase, *Anacystis nidulans* photolyase, and modified, non-native (e.g., recombinant) enzyme products thereof.

DNA repair enzymes may also include other members from the BER, NER or alternate pathways. These enzymes may include $O^6$-methylguanine-DNA methyltransferases, uracil- and hypoxanthine-DNA glycosylases, DNA exonucleases, damaged-bases glycosylases (e.g., 3-methyladenine-DNA glycosylase), endonucleases alone or in complexes (e.g., *E. coli* uvrA/uvrB/uvrC endonuclease complex), and other enzymes and enzyme complexes whose activities at present are only partially understood, such as, the products of the ERCC genes of humans and the RAD genes of yeast. Exemplary DNA repair enzymes include, but are not limited to, uracil DNA glycosylases, 3-methyladenine DNA glycosylase, Endonuclease III/thymine glycol DNA glycosylases, Endonuclease VIII, fapy/8-oxoguanine DNA glycosylases, A-G-mismatch DNA glycoslyases, G-T mismatch DNA glycosylases, formyluracil DNA glycoslyases, hydroxymethyl uracil DNA glycosylases, XPC-hHR23B, XPA, RPA, XPB, TFIIH, XPG, XPF-ERCC1, Rad4-Rad23, Rad14, Rfa, Rad25/Ss12, Rad3, Rad2, Rad1-Rad10, various DNA polymerases, DNA ligases and the like. Exemplary sources for these enzymes may include bacterial or mammalian cell sources, including, but not limited to *E. coli, S. cerevisiae, S. pombe*, human, human, monkey, mouse, rat, hamster and the like.

As used herein, the term "DNA repair enzyme" is intended to include the foregoing enzymes and other enzymes now known or subsequently discovered or developed, including glycosylases, apurinic/apyrimidinic endonucleases or other enzymes having activities capable of repairing damaged DNA.

DNA repair enzymes of the present invention may be derived or extracted from suitable sources such as *E. coli, Micrococcus*, and the like. The DNA repair enzymes may be encapsulated in liposomes as described in U.S. Pat. No. 5,296,231, the entire contents of which is incorporated herein by reference. For example, a DNA repair enzyme derived from a *Micrococcus luteus* cell lysate is provided in a liposomal formulation containing lecithin and water and is available as ULTRASOMES™ from Applied Genetics, Inc. Dermatics, Freeport, N.Y. or ULTRASOMES-V™ from Barnet Products Corporation, Englewood Cliffs, N.J. Liposomes encapsulating an *Anacystis nidulans* lysate containing the *Anacystis nidulans* photolyase are available as PHOTOSOMES™ from Applied Genetics, Inc. Dermatics, (Freeport, N.Y.). The liposomes may include conventional phospholipids, oleic acid and/or cholesterol hemisuccinate from vegetable-derived sources, e.g., soybean or they may be produced from other suitable sources conventionally known to those skilled in the art.

Exemplary embodiments may incorporate ULTRASOMES™, ULTRASOMES-V™, PHOTOSOMES™, or PHOTOSOMES-V™ in an amount ranging from about 0.01% to 20% by weight of the total composition, desirably from about 0.1 wt % to about wt 10%, more desirably from about 0.5 wt % to about 3 wt %.

Liposomes may be used as delivery agents to facilitate transfer of cosmetically active agents into the dermis of skin, such as the DNA repair enzymes or the plant or botanical ingredients of the present invention. Other delivery agents may be used for dermal delivery in place of the liposomes, including, but not limited to skin delivery vehicles known to those skilled in the art, including emulsions, microemulsions, nanoemulsions, nanoparticles, microspheres, ethosomes, transfersomes, and niosomes.

Additional cosmetic ingredients may also be included in the cosmetic composition of the present invention, including, but not limited to, ingredients present in: licorice, licorice extracts, licorice derivatives (e.g., glycyrrhizinates); lemon extract; cucumber extract; sunflower seed extract; castor seed oil; oat proteins, oat extracts, hydrolyzed oats; silk protein (e.g., sericin); hyaluronic acid and its derivatives (e.g., sodium hyaluronate); vitamins; minerals; anti-oxidants; phospholipids, sphingolipids, cholesterol; and/or other ingredients or combinations thereof having anti-aging, anti-oxidant, anti-inflammatory, anti-irritant, anti-cancer or other skin-protective properties; aesthetic appearance enhancing properties; and/or increased skin delivery properties.

Cosmetically useful vitamins, minerals and/or anti-oxidants for topical application in accordance with the present invention include plant ingredients and extracts having anti-oxidant properties (e.g., Rosemary extract, *Centella asiaticoside*, etc.); vitamin A and its precursors or derivatives (e.g., beta-carotene, retinyl palmitate); vitamin B3 and its precursors or derivatives (e.g., niacinamide); vitamin B5 and its precursors or derivatives (e.g. panthenol); vitamin C and its precursors or derivatives (e.g., tetrahexyldecyl ascorbate, ascorbyl palmitate); vitamin E and its precursors or derivatives (e.g., d-alpha-tocopherol, tocopheryl acetate); vitamin K and its precursors or derivatives; selenium and its derivatives (e.g., L-selenomethionine); and alpha lipoic acid (ALA).

ALA is a potent, naturally occurring anti-oxidant, sometimes referred to as the "universal anti-oxidant" because of its activity and solubility in both water and lipids. ALA is able to penetrate into skin cells, is able to prevent activation of the proinflammatory NF-kB pathway responsible for breakdown of collagen and elastin, and is able to boost the protective effects of vitamins E and C, thereby boosting naturally occurring anti-oxidants within cells.

In one embodiment, tetrahexyldecyl ascorbate may be incorporated in the composition of the present invention. Tetrahexyldecyl ascorbate is a stable, lipid-soluble ester derivative of vitamin C. Vitamin C has been reported to promote collagen synthesis, inhibit lipid breakdown, regenerate vitamin E, reduce fine lines and wrinkles, heal sunburns, and is a potent anti-oxidant scavenger of free radicals having significant anti-inflammatory properties, hindering production of e.g., arachidonic acid.

In another embodiment, panthenol or its equivalents are contemplated for use with this invention. Panthenol is an effective film-forming moisturizing agent having anti-inflammatory properties. Panthenol equivalents may include alcohol derivatives of pantothenic acid, such as the ones described in CTFA Cosmetic Ingredient Handbook, The Cosmetic, Toiletry and Fragrance Association. Inc., pp. 272-273, 1992. For optimal usefulness, the amount of panthenol should be chosen so that the composition dries reasonably quickly. The more panthenol in the composition, the longer it takes for the composition to dry when it is applied to skin or other surfaces.

Vitamins, minerals, and/or anti-oxidants may be present in a collective amount ranging from about 0.01% to 20% by weight of the total composition, desirably from about 0.1 wt % to about wt 10%, more desirably from about 0.5 wt % to about 3 wt %.

Optionally, the present composition may additionally include one or more anesthetics, anti-allergenics, anti-irritants, antifungals, anti-microbials, anti-inflammatory agents, antiseptics, chelating agents, colorants, depigmenting agents, emollients, emulsifiers, film formers, fragrances, humectants, insect repellents, lubricants, moisturizers, pharmaceutical agents, photostabilizing agents, preservatives, skin protectants, skin penetration enhancers, sunscreens, stabilizers, surfactants, thickeners, viscosity modifiers, or any combinations thereof.

The present invention provides plant or botanical ingredients and natural, active ingredients having anti-irritant or anti-inflammatory properties to counter potential irritation to skin. Although some embodiments lack the use of exfoliating agents, these agents may be included provided that sufficient anti-irritant/anti-inflammatory agents are included to ameliorate the irritating effects of exfoliating agents. Exemplary anti-irritants include, but are not limited to, aloe vera, α-bisabolol, caffeine or other xanthenes, chamomile, cola nitada extract, dipotassium glycyrrhizinate, glycyrrhizic acid and its derivatives, green tea extract, lecithin or hydrogenated lecithin, licorice extract, tea tree oil, steroidal or non-steroidal anti-inflammatory agents, including, but not limited to cyclooxygenase inhibitors (e.g., salicylic acid, acetylsalicylic acid), NF-κB inhibitors, strontium acetate, strontium chloride, strontium nitrate, urea, or combinations thereof. Desirable anti-irritants may include dipotassium glycyrrhizinate, lecithin and hydrogenated lecithin.

Anti-irritant or anti-inflammatory agents may be present individually or collectively in an amount ranging from about 0.01% to 10% by weight of the total composition, desirably from about 0.05 wt % to about wt 5%, more desirably from about 0.2 wt % to about 1.5 wt %.

The plant ingredients, plant extracts, oils, vitamins, minerals, antioxidants, anti-irritants or other active agents may be included, either individually or collectively, in a pharmaceutically or cosmetically acceptable vehicle. Examples of pharmaceutically or cosmetically acceptable vehicles suitable for the embodiments of the present invention include, but are not limited to, water, C1-C4 alcohols, fatty alcohols, fatty ethers, fatty esters, glycerin, glycols, vegetable oils, mineral oils, lecithin, hydrogenated lecithin, liposomes, laminar lipid materials, phospholipids, polyglycols, polyols, propyl alcohol, silicone oils, vegetable oil, or any combinations thereof.

The pharmaceutically or cosmetically acceptable vehicle of the present invention may be in the form of a homogeneous phase formulation or in the form of an emulsion or microemulsion including, but not limited to, oil-in-water, water-in-oil and multiple including triple, phase emulsions. These emulsions can cover a broad range of consistencies including thin lotions (which can also be suitable for spray or aerosol delivery), creamy lotions, light creams and heavy creams. Other suitable topical carriers include anhydrous liquid solvents such as oil and alcohol; aqueous-based single phase liquid solvent (e.g., hydro-alcoholic solvent system); anhydrous solid and semisolid (such as gel and stick); and aqueous based gel and mousse system.

The pharmaceutically or cosmetically acceptable vehicle will usually contain from about 5% to about 99.9% by weight of the total composition, desirably from about 25% to about 80%, and more desirably from about 50% to about 70% by weight of the composition, and may, in the absence of other cosmetic adjuncts, form the balance of the composition.

Emollients are moisturizers to maintain hydration or to rehydrate the skin by providing a protective emollient coating. Emollients may be classified under such general chemical categories as esters, fatty acids and alcohols, polyols and hydrocarbons. Esters may be mono- or di-esters. Representative examples of fatty di-esters include, but are not limited to, dipotassium glycyrrhizinate, dibutyl adipate, diethyl sebacate, diisopropyl dimerate, and dioctyl succinate. Acceptable branched chain fatty esters include, but are not limited to, 2-ethyl-hexyl myristate, isopropyl stearate and isostearyl palmitate. Acceptable tribasic acid esters include, but are not limited to, triisopropyl trilinoleate and trilauryl citrate. Acceptable straight chain fatty esters include, but are not limited to, lauryl palmitate, myristyl lactate, and stearyl oleate.

Suitable fatty alcohols and acids may include, but are not limited to, alcohols or acids having from about 10 to 20 carbon atoms. For example, alcohols such as cetyl, myristyl, palmitic and stearyl alcohols and acids may be used.

Polyols may serve as emollients, including, but not limited to linear and branched chain alkyl polyhydroxyl compounds. Representative polyols, include, but are not limited to butylene, propylene glycol, sorbitol, glycerin, polymeric polyols, such as polypropylene glycol and polyethylene glycol, and the like.

Hydrocarbons may serve as emollients and may include hydrocarbon chains having from about 12 to 30 carbon atoms, including, but not limited to mineral oil, petroleum jelly, squalene and isoparaffins.

Exemplary emollients include, but are not limited to, butylene, caprylic/capric triglyerides, castor oil, ceteareth-20, ceteareth-30, cetearyl alcohol, ceteth 20, cetostearyl alcohol, cetyl alcohol, cetyl stearyl alcohol, cholesterol, cocoa butter, diisopropyl adipate, glycerin, gyceryl monooleate, glyceryl monostearate, glyceryl stearate, isoparaffins, isopropyl myristate, isopropyl palmitate, lanolin, lanolin alcohol, hydrogenated lanolin, isoparaffins, liquid paraffins, linoleic acid, mineral oil, oleic acid, petroleum jelly, phospholipids, polyethylene glycol, polyethylene glycol-7 glyceryl cocoate, polyethylene glycol-18 methyl ester dimethyl silane, polyoxyethylene glycol fatty alcohol ethers, polyoxypropylene 15-stearyl ether, polypropylene glycol propylene glycol, propylene glycol stearate, sorbitol, sphingolipids, squalene, steareth-2 or -100, stearic acid, stearyl alcohol, urea, white petrolatum, and the like.

Emollients may be present individually or collectively in an amount ranging from about 0.005% to 20% by weight of the total composition, desirably from about 0.1 wt % to about wt 10%, more desirably from about 10.0 wt % to about 5.0 wt %.

Humectants are moisturizers that can bind water and retain it on the skin surface. Exemplary humectants include, but are not limited to, acetyl glucosamine, bisaccharide gum, butylene glycol, ethoxydiglycol, ethylene glycolpolypropylene, glucose, glycereth-26, glycerin, glycerol, glycol, lactitol, maltitol, propylene glycol, sericin, sodium hyaluronate, sorbitol, xylitol, sodium citrate, glucose and the like.

Humectants may be collectively present in an amount ranging from about 0.1% to 40% by weight of the total composition, desirably from about 2.5 wt % to about wt 25%, more desirably from about 5 wt % to about 15 wt %.

The present compositions may provide one or more preservatives. Suitable preservatives include disodium EDTA, benzyl alcohol, methylparaben, phenoxyethanol, propylparaben, ethylparaben, butylparaben and isobutylparaben.

Another category of functional ingredients within the cosmetic compositions of the present invention are thickeners. Thickeners will usually be present in a collective amount ranging anywhere from about 0.01 to 10% by weight, desirably from about 0.05 to 5% by weight, more desirably from about 0.1% to 1% by weight of the composition. Exemplary thickeners are cross-linked polyacrylate materials. Gums such as xanthan, carrageenan, gelatin, karaya, pectin and locust bean gum may be used. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The compositions of the present invention may be formulated in any convenient form suitable for topical application to the skin. Such product forms include, but are not limited to, aerosol spray, cream, dispersion, emulsion, foam, gel, liquid, lotion, mousse, ointment, patch, pomade, powder, pump spray, solid, solution, stick, and towelette. A desired cosmetic form is a cream that is an oil-in-water emulsion. Water-in-oil and water-in-silicone emulsions also are contemplated.

In one embodiment, the present invention provides a cosmetic treatment system including a patch impregnated with the topical composition of the present invention. Patches for use in the present invention may come in any shape suitable for treating a particular target area. The patch may encompass a small area targeting a particular area or it may cover a large area, such as a face in the form of a mask. The overall size and geometry of current patches for applying medicaments around the eyes can make it difficult to apply eye treatment products in close proximity to the eye.

Figure 9:
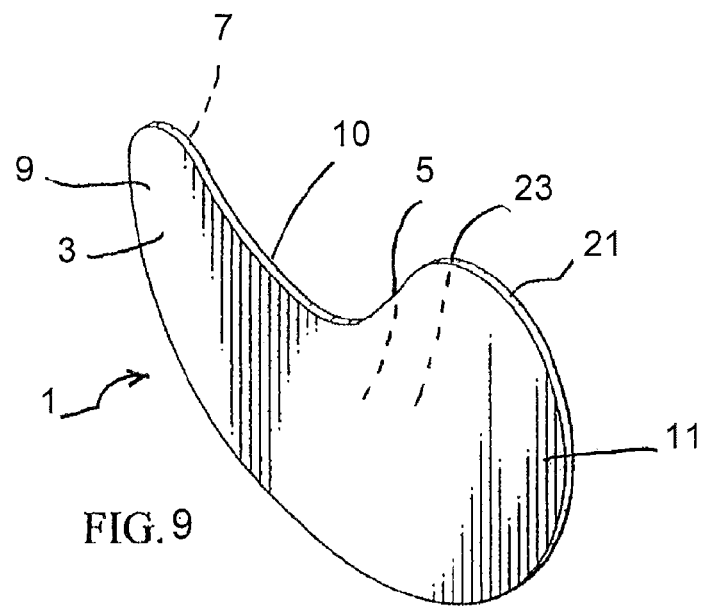
FIG. 9 shows a representative patch for treating an area around the eye.

FIG. 9 depicts a representative patch 1 of the present invention. The patch includes a front side 3 and a back side 7 impregnated with the topical composition 5. When treating the eye area, the patch 1 may be kidney-shaped with convex ends, a smaller radiused first end 9, and a larger radiused second end 11 opposite the first end 9 with a top portion 10 having a surface that is substantially parallel to the curvature of the cheekbone adjacent to a subject's eye. The relatively shorter, more radiused design of the eye patch 1 depicted in FIG. 9 makes it easier for a subject 13 to position the patch 1 in close proximity to the eye 15, both under the eye 17 and near the side of the eye 19. However, for treatment of the area around the eye, the length, width, and geometry of the patch 1 set forth in e.g., FIG. 9 may be varied without negatively impacting its effectiveness. Moreover, the present invention may include a pair of patches 1 for treating each eye 15 individually, or it may contain a single, continuous patch for treating both eyes at once. A patch 1 for use with the present invention may be further adapted, fitted and/or cut in accordance to the particular contours or shape of the area to be treated. A skilled artisan will of course recognize that the front side 5 or the back side 7 of patch 1 may be impregnated with the topical composition 5, depending on the orientation of the patch 1 or the particular eye that is being treated.

The patch 1 may be made of any removal material suitable for absorbing, containing, and releasing compositions of the present invention. For example, the patch 1 may be made of non-woven material. The non-woven material may include cotton, cotton/polyester blends, or other suitable combinations of natural or synthetic materials. The patch may be further adapted to provide an occlusive, semi-occlusive or non-occlusive barrier. The patch may be adhesive or non-adhesive. As depicted in FIG. 9, the patch 1 may include a single layer of material 21 or it may include multiple layers of the same and/or dissimilar materials to provide additional structural integrity and/or flexibility. Suitable patches or patch materials are disclosed in e.g., U.S. Pat. No. 6,096,334; U.S. Pat. No. 6,120,792; U.S. Pat. No. 6,495,158; U.S. Pat. No. 6,623,751; U.S. Pat. Appl. No. 2002/0086043; U.S. Pat. Appl. No. 2003/0152610; U.S. 2003/0175328; and references cited therein, the contents of which are incorporated herein by reference.

The topical composition 5 may be coated onto at least a portion of the patch 1 immediately prior to applying the patch 1 to a subject 13. Alternatively, the patch 1 may be pre-coated with the topical composition and ready for use. Preferably, the topical composition 5 is applied to substantially the entire surface back 7 of the patch 1. The patch 1 and/or the topical composition 5 may further include an adhesive 23. The adhesive 23 may be applied to the back 7 of the patch 1 prior to or subsequent to applying the topical composition 5 to the patch 1. The adhesive 23 may be any adhesive known to those skilled in the art and suitable for removably adhering the patch and/or topical composition to a substrate, such as human skin. The adhesive may be applied to the front side 5 or the back side 7 of patch 1, depending on the orientation of the patch 1 or the particular side impregnated with the topical composition.

The cosmetic treatment system of the present invention may include a packaging system for holding the individual components of the cosmetic treatment system. In a preferred embodiment, the cosmetic treatment system includes a patch; at least one container; and a topical composition formulated for treatment of an area in close proximity to the eye.

Figure 11:
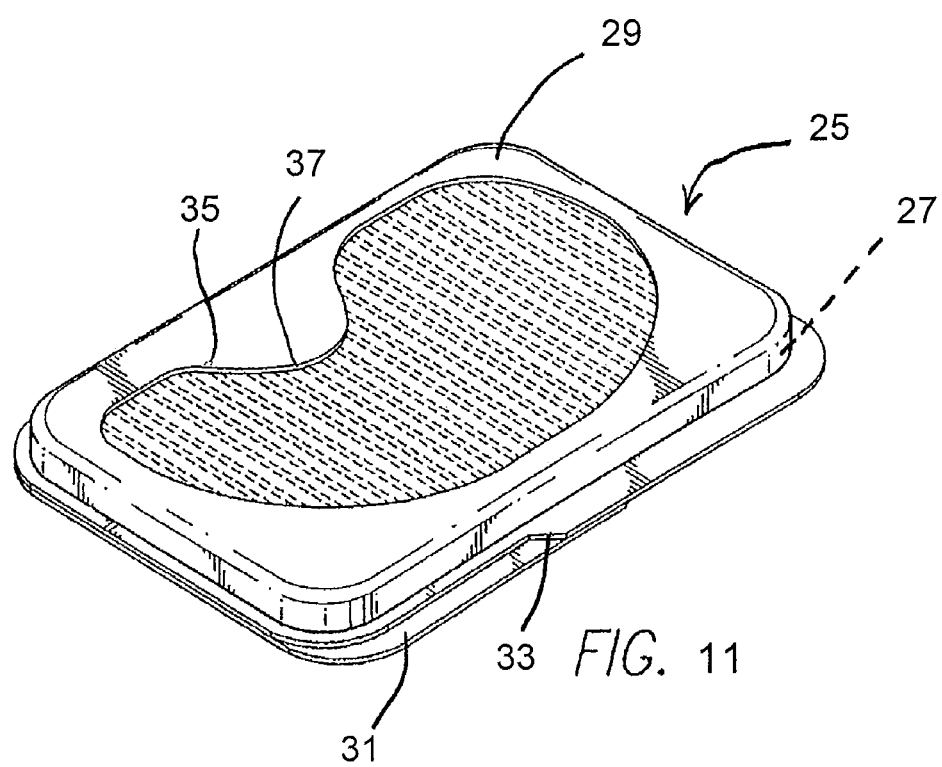
FIG. 11 shows a representative container for holding the patch of FIG. 9.

One or more containers may be used to hold one or more of the components of the cosmetic treatment system. Any container(s) suitable for holding the components of the cosmetic treatment system may be used in accordance with conventional practices known to those skilled in the art. FIG. 11 depicts a representative container 25 adapted for holding the patch 1. The rectangular container 25 includes an interior 27, a top cover 29 and a base portion 31. The top cover 29 may include an indent 33 for opening or separating the top cover 29 from the base portion 31, to facilitate retrieval of the patch 1 held in place by a sunken cavity having a sufficient depth 35 and shape 37 complementarily adapted for securely holding the patch 1 of FIG. 9 in the base portion 31. Alternatively, the patch may be packaged in a container in the form of a sunken tray overlayed with a sealably removable cover to securely maintain the patch in the sunken tray prior to use.

Figure 10:
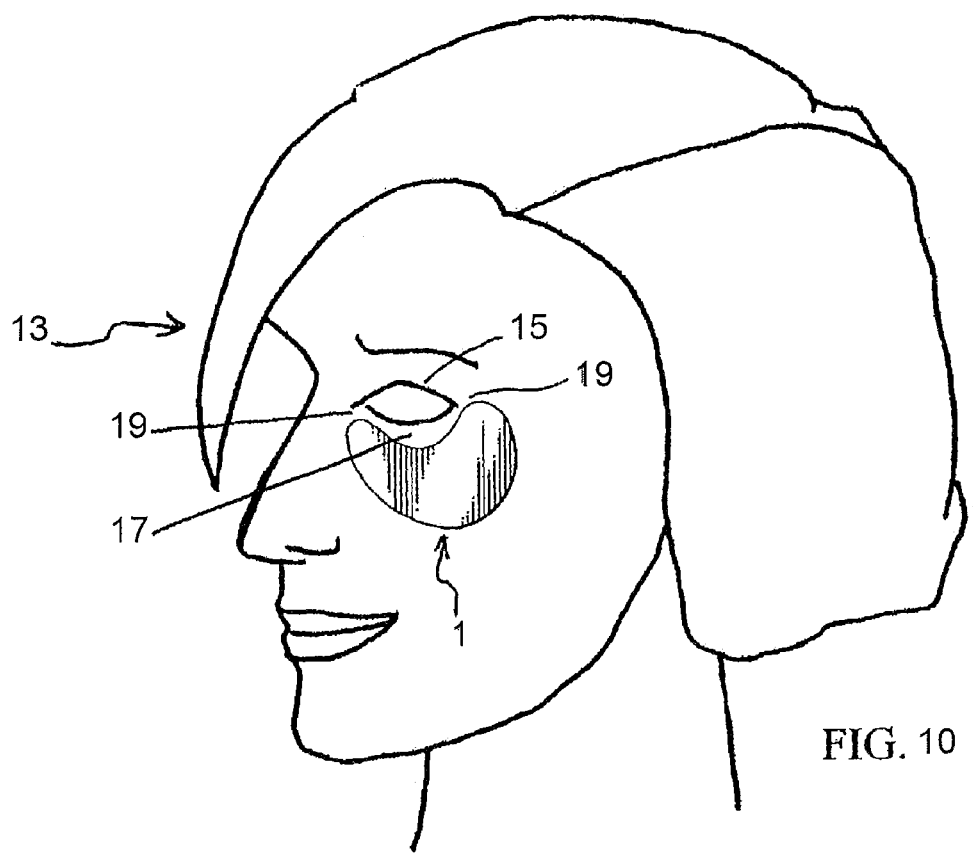
FIG. 10 shows the patch of FIG. 9 affixed to a portion of a subject's face under the subject's left eye.

The container may be prepared by thermoforming or by thin-wall injection molding of a suitable material, such as polypropylene. The design of the container 25 can be modified and adapted to the shape of the particular patch. The container 25 may be formulated for holding only the patch or it may be formulated to hold the patch 1, as well as the other components of the cosmetic treatment system, including the topical composition 5 and/or an adhesive 23 for promoting the adherence of the topical composition 5 and/or patch 1 to a subject 13 as exemplified in FIG. 10. Suitable containers for holding patches of the present invention are disclosed in U.S. Pat. No. 6,623,751, the contents of which are incorporated herein by reference.

Topical composition(s) of the present invention may be packaged in a suitable container to suit its viscosity and intended use by the consumer. For example, a lotion or a cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The present invention also contemplates a cosmetic treatment system including a packaging system containing a suitable amount of the cosmetic composition suitable for a desired period of time, such as fourteen days. According to this embodiment, the cosmetic treatment system includes a packaging system containing a plurality of containers, with each container having an amount of the cosmetic composition according to the present invention suitable for a single use. The container may be in the form of a vial or other suitable holding device.

In one embodiment, the cosmetic treatment system includes a packaging system having a plurality of vials, each vial containing a sufficient amount of the cosmetic composition of the present invention suitable for a single application of the cosmetic composition to the skin. The packaging system may be formulated to provide a number of vials matching the number of days in which the cosmetic composition is applied to skin. Alternatively, the packaging system may be formulated for more than one application per day. In one embodiment, the packaging system may contain 14 vials for daily treatment to skin over a period of 14 days. The packaging system may further contain one or more applicators for applying the compositions and may further include a set of instructions for use of the packaging system associated with the cosmetic treatment system.

The present invention also includes methods of treating skin by topically applying the cosmetic compositions of the present invention. In use, a small quantity of the composition, for example from 1 to 100 ml, may be applied to exposed areas of the skin, from a suitable container or applicator and, if necessary, it is then spread over and/or rubbed into the skin using the hand or fingers or a suitable device. Alternatively, the composition may be applied to the skin in the form of a patch that has been impregnated with the composition. The patch may be made of non-woven material and may further contain an adhesive to adhere the patch to the skin.

In one embodiment, the present invention provides a method for preventing, arresting, reversing, ameliorating, diminishing, reducing or improving a sign of aging, in which a composition of the present invention is topically applied to skin in a cosmetically effective amount sufficient to prevent, arrest, reverse ameliorate, diminish, reduce or improve a sign of aging in skin. Exemplary signs of aging include, but are not limited to, facial lines, fine lines, wrinkles, crow's feet, dark eye circles, blemishes, age spots, stretch marks, or combinations thereof.

In another embodiment, the present invention provides a method for improving the aesthetic appearance of skin, in which a composition of the present invention is topically applied to skin in a cosmetically effective amount sufficient to improve the aesthetic appearance of the skin. The improvements may relate to skin thickness, elasticity, resiliency, moisturization, tone, texture, radiance, luster, brightness, clarity, contour, firmness, tautness, suppleness, softness, sensitivity, pore size, or combinations thereof.

The improvements may further relate to improving adverse skin conditions affected by, resulting in or resulting from the group consisting of psoriasis, eczema, seborrhea, dermatitis, sunburn, estrogen imbalance, hyperpigmentation, hypopigmentation, discoloration, yellowing, freckles, skin atrophy, skin breakout, skin fragility, dryness, chapping, sagginess, thinning, hyperplasia, fibrosis, enlarged pores, cellulite formation, bruising, acne formation, apoptosis, cellular differentiation, cellular de-differentiation, prevention of tumor induction or tumor progression, viral infections, fungal infections, bacterial infections, spider veins (telangectasia), hirsutism, rosacea, pruritis, calluses, warts, corns, or combinations thereof.

The signs of aging or adverse skin conditions may result from free radical damage, environmental agents, pollutants, diet, chronological aging, premature aging, hormonal aging, photo-aging, or combinations thereof. Accordingly, the present compositions and methods selected for improved anti-aging characteristics or adverse skin conditions may employ topical application of active ingredients inhibiting enzymes or mediators that accelerate or facilitate aging, damage, formation of free radicals, or breakdown of skin elements, including, but not limited to metalloproteinases, collagenases, elastases, hyaluronidases, and proteases. The active ingredients may have anti-oxidant activity, free radical scavenging or anti-inflammatory activity and/or they may inhibit breakdown of collagen, elastin, fibronectin, hyaluronic acid, glycosaminoglycans (GAG) or other extracellular matrix elements or regulatory enzymes or mediators of the NF-kB signal transduction pathway. The active agents may also inhibit other signal transduction pathways associated with aging, including the mediators and regulators associated with these pathways, or combinations thereof.

In addition to improving the aesthetic or cosmetic appearance of skin, the topical compositions of the present invention may be topically applied to enhance the general health, vitality and appearance of the skin. For example, the present composition may be applied to skin to improve microcirculation, communication among skin cells, replenishment of essential nutrients or skin constituents, or to improve the metabolism, proliferation, multiplication, turnover and/or exfoliation of skin cells.

Exfoliation may be carried out with or without the use of alpha- or beta hydroxy acids or other exfoliants, or combinations thereof by topical application to skin. When using exfoliating agents in the compositions of the present invention, sufficient anti-irritant or anti-inflammatory agents are included to neutralize the potential irritation associated with exfoliating agents in the absence of such neutralizing agents.

The following are non-limiting examples of the present invention. Unless indicated otherwise, all proportions and percentages are by weight.

EXAMPLE 1

The following are examples of formulations according to the present invention.

TABLE 1

| Ingredients | Amount (percent) |
|---|---|
| Rosemary leaf extract | 0.01-0.5 |
| *Centella asiatica* extract | 0.01-0.08 |
| *Echinacea angustifolia* extract | 0.005-0.02 |
| *Alpinia speciosa* leaf extract | 0.01-0.08 |
| Ultrasomes ™ | 0.05-3.0 |
| Other plant ingredients | 0.1-2.0 |
| Vitamins | 0.1-3.0 |
| Preservatives | 0.5-2.0 |
| Humectants | 10.0-25.0 |
| Anti-Irritants | 0.2-1.5 |
| pH Adjuster | 0.2-1.0 |
| Thickener | 0.05-1.5 |
| Emollient | 1.0-5.0 |
| Water | q.s. |

The formulation shown in Table 1 may be provided in small quantities and applied directly to the face over a periodic basis.

TABLE 2

| Ingredients | Amount (percent) |
|---|---|
| Rosemary leaf extract | 0.01-5.0 |
| *Alpinia speciosa* leaf extract | 0.01-5.0 |
| Ultrasomes ™ | 0.05-3.0 |
| Other plant ingredients | 0.1-2.0 |
| Vitamins | 0.1-3.0 |
| Preservatives | 0.5-2.0 |
| Humectants | 10.0-25.0 |
| Anti-Irritants | 0.2-1.5 |
| pH Adjuster | 0.2-1.0 |
| Thickener | 0.05-1.5 |
| Emollient | 1.0-5.0 |
| Water | q.s. |

The formulation shown in Table 2 may be provided in small quantities in a patch and applied under the eyes over a periodic basis.

TABLE 3

| Ingredients | Amount (percent) |
|---|---|
| Rosemary leaf extract | 0.01-5.0 |
| *Alpinia speciosa* leaf extract | 0.01-5.0 |
| Ultrasomes ™ | 0.05-3.0 |
| *Avena sativa* kernel extract | 0.01-5.0 |
| Evening primrose seed extract | 0.01-5.0 |
| L-ergothioneine | |
| Hydrolyzed soy protein | 0.01-5.0 |
| Yeast protein | 0.01-5.0 |
| *Lentinus enodes* extract | 0.01-5.0 |
| *Nymphaea alba* flower extract | 0.01-5.0 |
| *Perilla frutescens* leaf extract | 0.01-1.0 |
| Vitamins | 0.1-3.0 |
| Preservatives | 0.5-2.0 |
| Humectants | 10.0-25.0 |
| Anti-Irritants | 0.2-1.5 |
| pH Adjuster | 0.2-1.0 |
| Thickener | 0.05-1.5 |
| Emollient | 1.0-5.0 |
| Water | q.s. |

The formulation shown in Table 3 may be provided in small quantities in a patch and applied under the eyes over a periodic basis.

EXAMPLE 2

The composition of Table 1 in Example 1 was tested in the following manner. Females between the age of 35 and 70, who were currently using a facial regimen consisting of a cleanser, toner and moisturizer twice-daily, who perceived themselves as having normal-to-dry or dry facial skin, and who had mild to moderate fine lines in the left periocular area (as determined by clinical grading) were chosen as test subjects. The test subjects were to continue use of their regular brands of skin care products, to not begin use of new skin or hair care products, and to avoid sun exposure (including tanning beds) and swimming pools for the duration of the study.

The test subjects were to use their normal facial skin care regimen (cleanser, toner and moisturizer twice-daily) and then to apply the composition of Table 1 of Example 1 after use of the toner and prior to the use of the moisturizer. The subjects were to use the composition daily for fourteen days and to be clinically evaluated at the start (day 1) and on days 4, 7, 10, and 14. During each evaluation, the clinician evaluated the skin for (1) the presence of mild to moderate fine lines, (2) tactile roughness, (3) clarity, (4) dryness/scaling. Each attribute was grading according to the following scale:

Fine lines (0 = none and 10 = severe)
Tactile Roughness (0 = smooth and 10 = rough)
Clarity (0 = dull, matte appearance and 10 = bright, luminous appearance)
Dryness/scaling (0 = moist and 10 = severe dryness).

In addition, corneometer measurements were taken to evaluate the moisture content in the left cheek skin at Baseline and at Days 4, 7, 10 and 14. The corneometer (CM 825) was placed on the cheek, in line with the center of the eye, on the ocular bone. Triplicate measurements were taken. The corneometer quantifies moisture content in the stratum corneum (SC) by an electrical capacitance method. The measurement has no units, but is proportional to the dielectric constant of the surface layers of the skin, and increases as the skin becomes more hydrated. The readings are directly related to the skin's electrical capacitance (picoFarads).

Figure 1B:
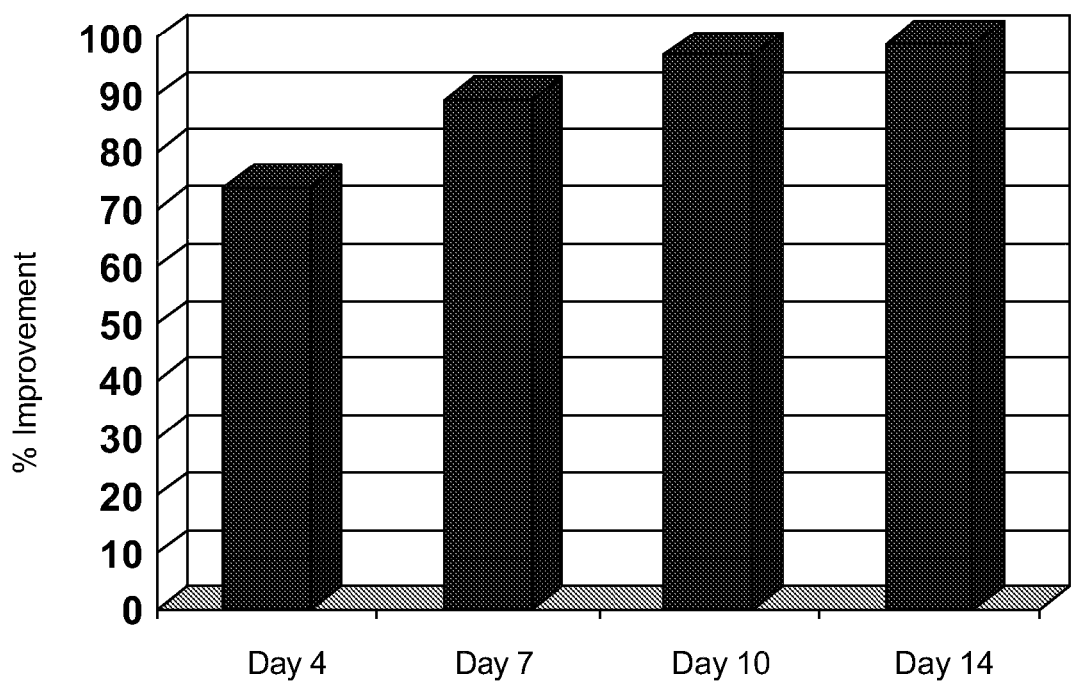
FIG. 1*b* is a graph depicting a reduction of fine skin lines when a representative composition of the present invention was topically applied to the skin over a 14 day period.

FIG. 1a shows the reduction in fine lines over a 14 day period during which a composition of Example 1 was applied daily to 62 test subjects. The y-axis depicts mean score changes for the 62 test subjects at the time of evaluation (at Baseline and at Days 4, 7, 10 and 14). As reflected in FIG. 1a, the Day 14 score represented a scoring change of −4.8 relative to the Baseline score. FIG. 1b is a graph that depicts the % improvement in fine lines expressed in % reduction in fine lines over the 14 day period during which a composition of Example 1 was applied daily. The graph illustrates a >70% reduction in fine lines by Day 4 and a 99% reduction in fine lines by Day 14.

Figure 2A:
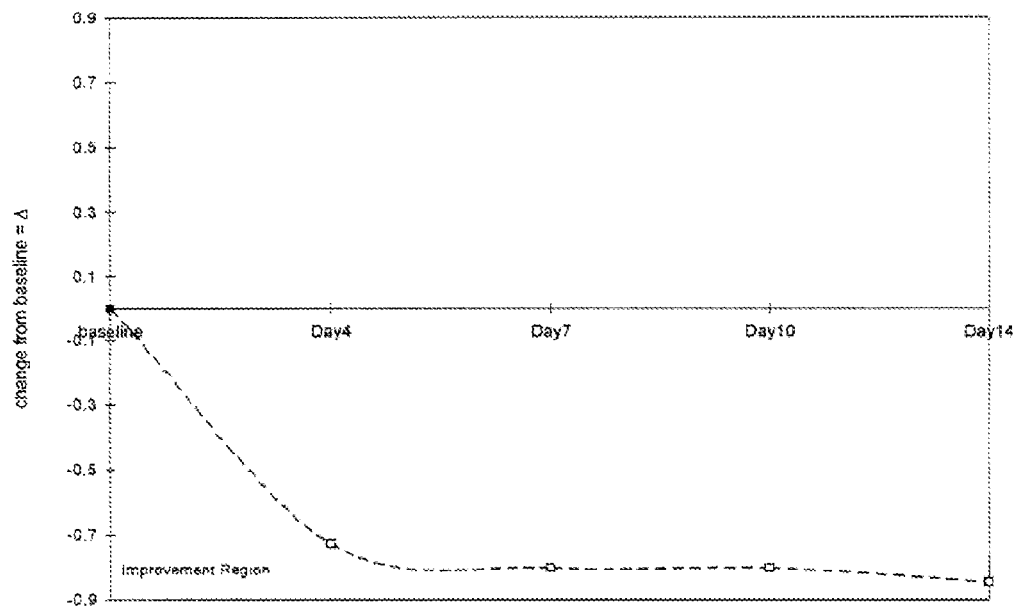
FIG. 2*a* is a graph depicting improved skin smoothness (i.e. a reduction in tactile roughness) when a representative composition of the present invention was topically applied to the skin over a 14 day period.
Figure 2B:
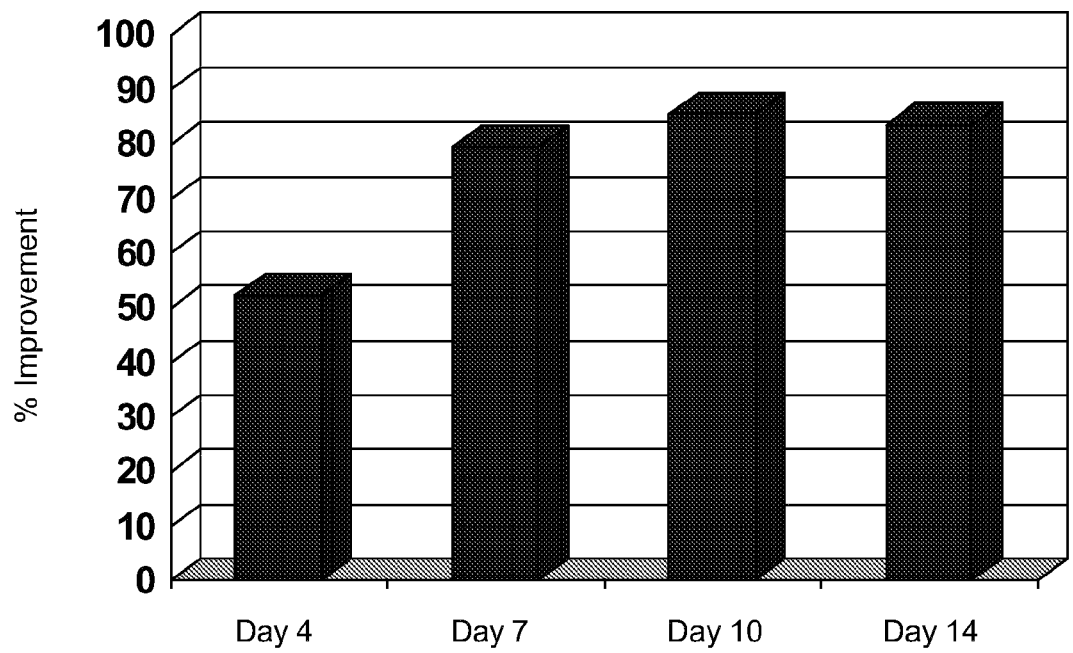
FIG. 2*b* is a graph depicting improved skin smoothness (i.e. a reduction in tactile roughness) when a representative composition of the present invention was topically applied to the skin over a 14 day period.

FIG. 2a shows the reduction in skin tactile roughness over a 14 day period during which a composition of Example 1 was applied daily. The y-axis depicts the change in scores between the Baseline and Days 4, 7, 10 and 14 (Baseline score minus score upon evaluation). As reflected in FIG. 2a, the Day 14 score represented a scoring change of −0.85 relative to the Baseline score. FIG. 2b is a graph that depicts the % improvement in skin smoothness expressed in % reduction in skin tactile roughness over the 14 day period during which a composition of Example 1 was applied daily. The graph illustrates a >50% reduction in tactile roughness by Day 4 and a >80% reduction by Days 10-14.

Figure 3A:
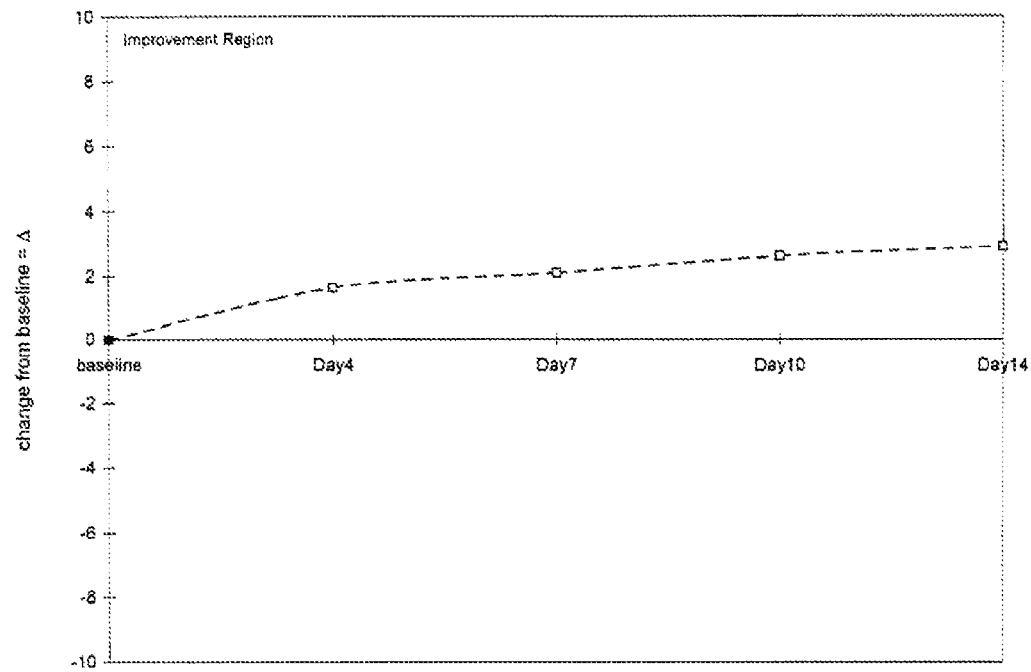
FIG. 3*a* is a graph depicting improved skin clarity when a representative composition of the present invention was topically applied to the skin over a 14 day period.
Figure 3B:
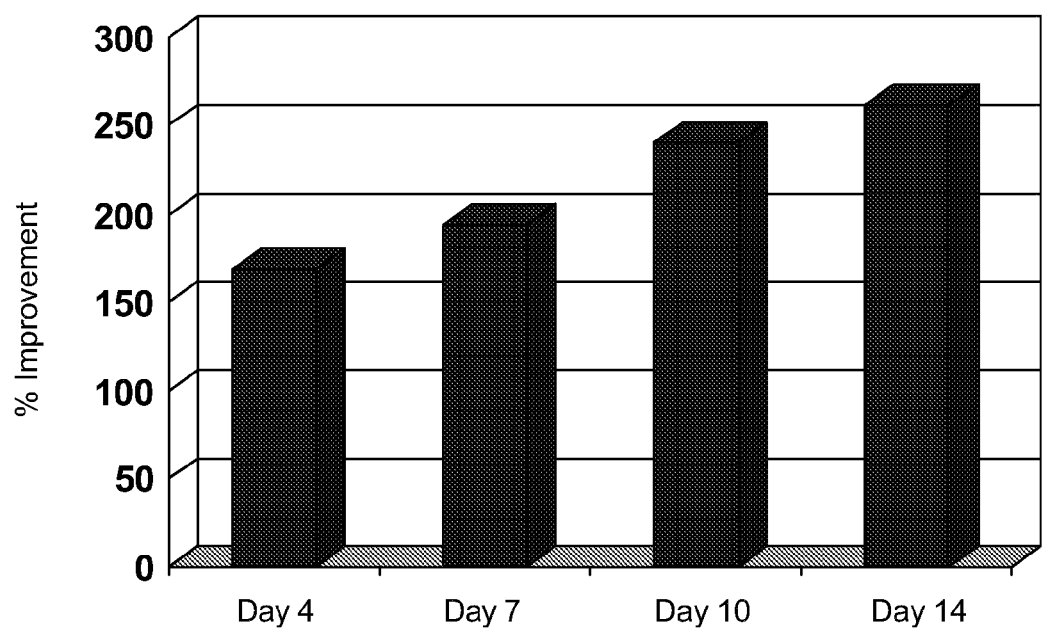
FIG. 3*b* is a graph depicting improved skin clarity when a representative composition of the present invention was topically applied to the skin over a 14 day period.

FIG. 3a shows the increase in skin clarity over a 14 day period during which a composition of Example 1 was applied daily. The y-axis depicts the change in scores between the Baseline and Days 4, 7, 10 and 14 (Baseline score minus score upon evaluation). As reflected in FIG. 3a, the Day 14 score represented a scoring change of 2.91 relative to a Baseline score. FIG. 3b is a graph that depicts the % improvement in skin clarity expressed in % increase in skin clarity over the 14 day period during which a composition of Example 1 was applied daily. The graph illustrates a >150% increase in skin clarity by Day 4, and >250% increase in skin clarity by Day 14.

Figure 4A:
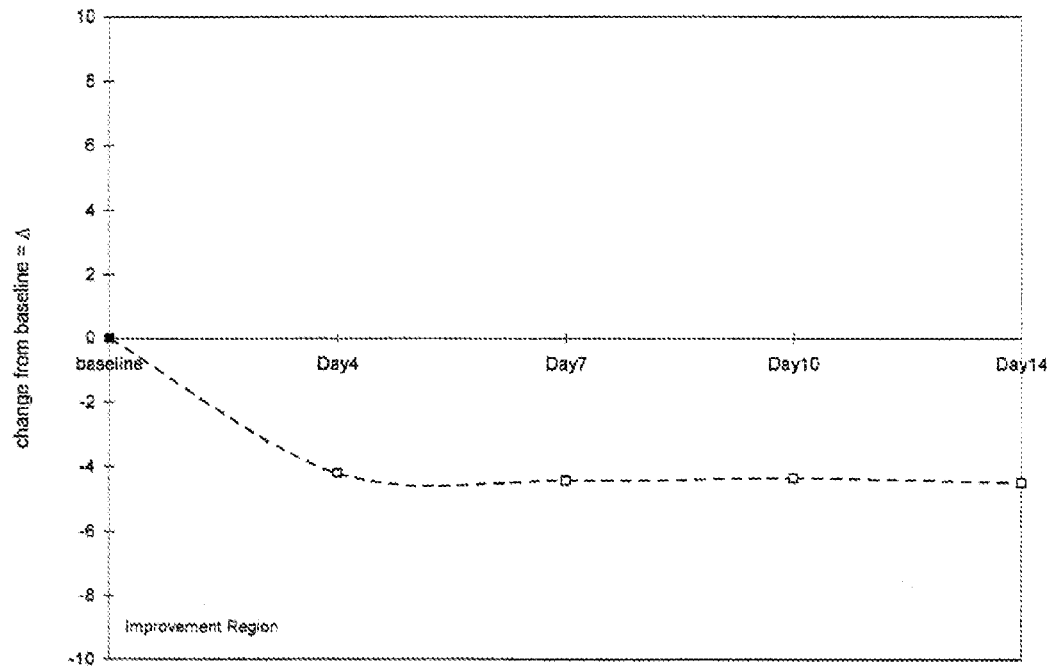
FIG. 4*a* is a graph depicting reduced skin dryness when a representative composition of the present invention was topically applied to the skin over a 14 day period.
Figure 4B:
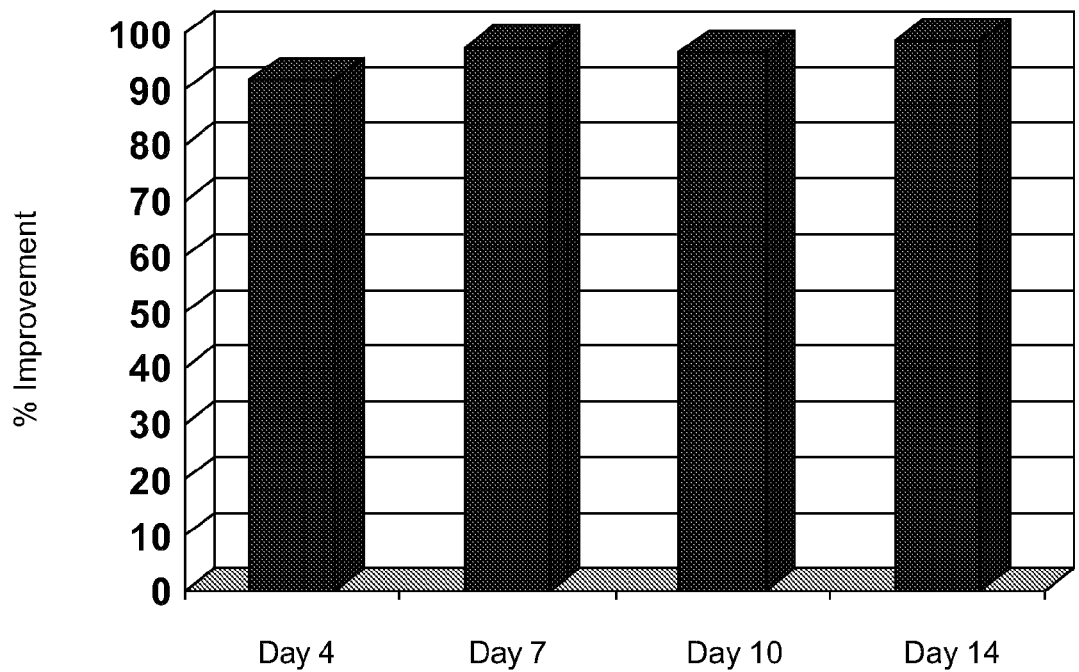
FIG. 4*b* is a graph depicting reduced skin dryness of skin when a representative composition of the present invention was topically applied to the skin over a 14 day period.

FIG. 4a shows the reduction in skin dryness over a 14 day period during which a composition of Example 1 was applied daily. The y-axis depicts the change in scores between the Baseline and Days 4, 7, 10 and 14 (Baseline score minus score upon evaluation). As reflected in FIG. 4, the Day 14 score of 0.06 represented a scoring change of −4.50 relative to the Baseline score. FIG. 4b is a graph that depicts the % improvement in skin dryness expressed in % reduction in skin dryness over the 14 day period during which a composition of Example 1 was applied daily. The graph illustrates a >90% reduction in fine lines by Day 4 and a 99% reduction in fine lines by Day 14.

Figure 5A:
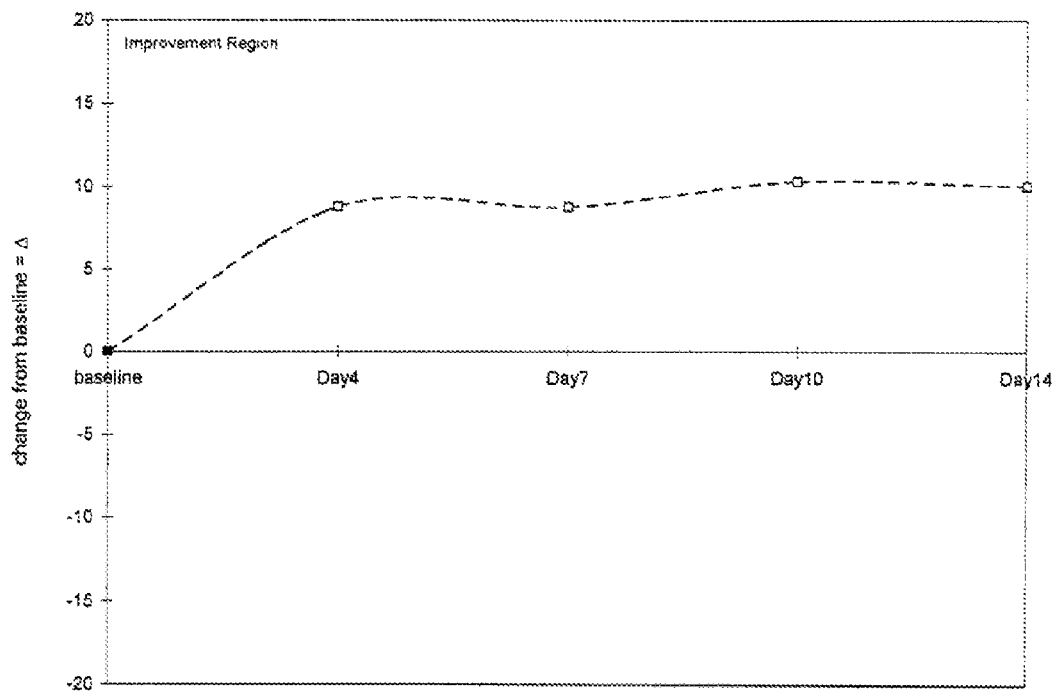
FIG. 5*a* is a graph depicting increased skin moisturization when a representative composition of the present invention was topically applied to the skin over a 14 day period.
Figure 5B:
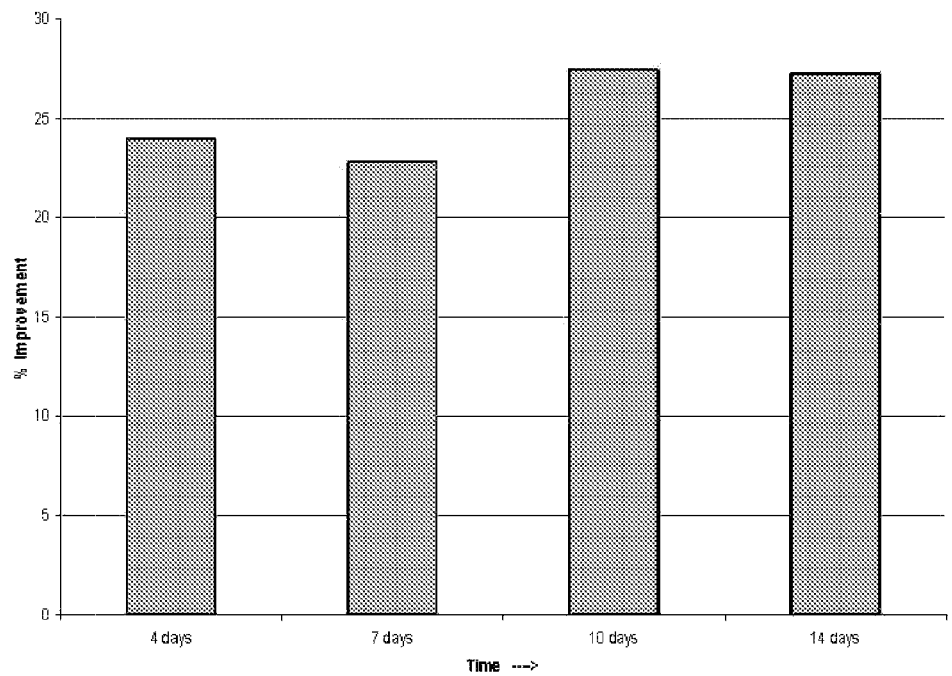
FIG. 5*b* is a graph depicting % moisturization when a representative composition of the present invention was topically applied to the skin over a 14 day period.

FIG. 5a shows the increase in skin moisture content over a 14 day period during which a composition of Example 1 was applied daily. The y-axis depicts the change in scores between the Baseline and Days 4, 7, 10 and 14 (Baseline score minus score upon evaluation). As reflected in FIG. 5a, the Day 14 score represented a scoring change of 10.04 relative to the Baseline score. FIG. 5b is a graph depicting % moisturization when a representative composition of the present invention was topically applied to the skin over a 14 day period.

Figure 6A:
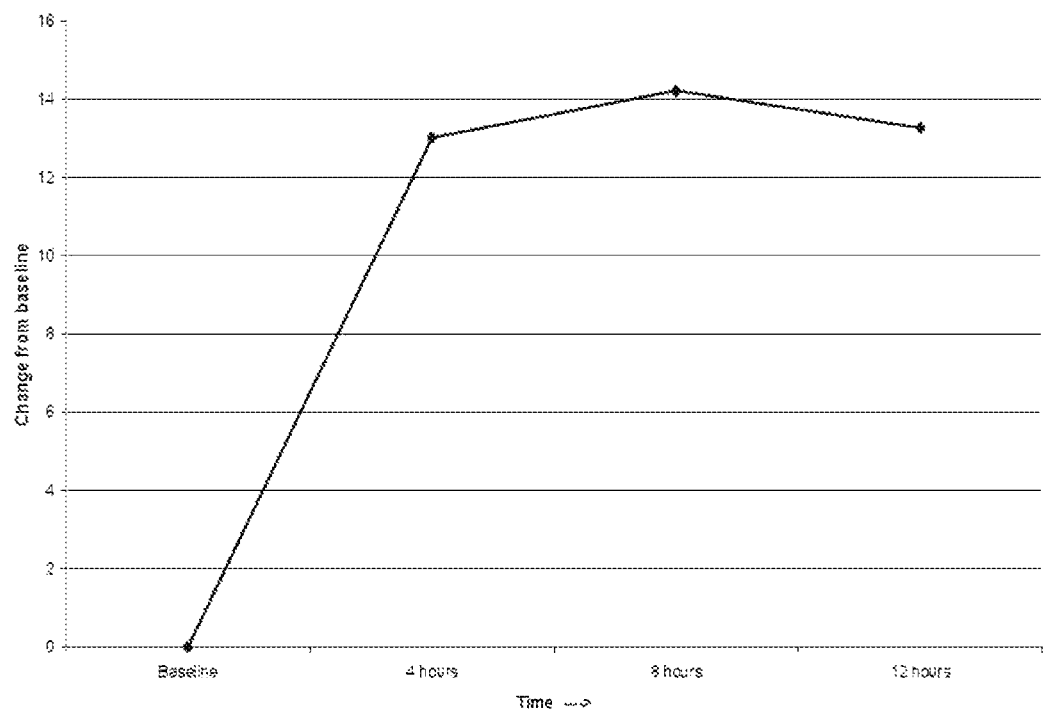
FIG. 6*a* shows the increase in skin moisture content when a representative composition of the present invention was topically applied to the skin over a 12 hour period.
Figure 6B:
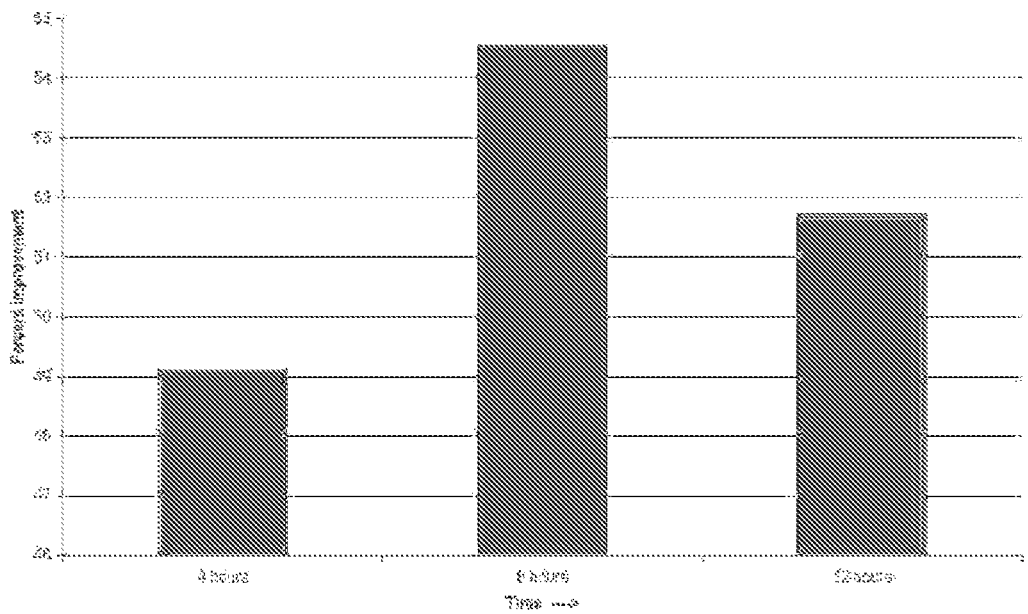
FIG. 6*b* is a graph depicting the % improvement in skin moisture content when a representative composition of the present invention was topically applied to the skin over a 12 hour period.

FIG. 6a shows the increase in skin moisture content over a 12 hour period in which a composition of Example 1 was applied immediately following Baseline measurements. The y-axis depicts the change in score between the Baseline (i.e., initial) and the 4, 8, and 12 hour measurements. FIG. 6b is a graph depicting the % improvement in skin moisture content expressed in % improvement in moisturization over a 12 hour period during which a composition of Example 1 was applied immediately following Baseline measurements. This graph illustrates a greater than 25% increase in moisturization after 12 hours.

FIG. 7a is a photograph of a portion of a subject's face before daily application of the composition of Table 1 of Example 1. FIG. 7b is a photograph of a portion of the subject's face after daily application of a composition of Table 1 of Example 1 over a period of fourteen days. It can be seen that application of the composition of Table 1 of Example 1 resulted in a reduction in fine lines.

FIG. 8a is a photograph of a portion of another subject's face before application of the before daily application of the composition of Table 1 of Example 1. FIG. 8b is a photograph of a portion of the subject's face after daily application of a composition of Table 1 of Example 1 over a period of fourteen days. It can be seen that application of the composition of Example 1 again resulted in a reduction in fine lines.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

The invention claimed is:

1. A method of improving the appearance of skin or at least one sign of aging in the skin, the method comprising topically applying to the skin a composition in a cosmetically effective amount sufficient to improve the appearance of the skin or the at least one sign of aging in skin, wherein the composition comprises
   a. a plant ingredient or a plant extract from *Rosmarinus officinalis* selected from the group consisting of a plant extract, an ursolic acid, a carnosic acid, a rosmarinic acid, an oleanolic acid, and combinations thereof;
   b. at least one plant ingredient or plant extract from each of
      i. *Centella asiatica*, wherein the at least one plant ingredient or plant extract from *Centella asiatica* is selected from the group consisting of a plant extract, an asiatic acid, a madecassic acid, an asiaticoside, and combinations thereof;
      ii. *Echinacea angustfolia*, wherein the at least one plant ingredient or plant extract from *Echinacea angustfolia* is selected from the group consisting of a plant extract and an echinoside; and
      iii. *Alipinia speciosa*, wherein the at least one plant ingredient or plant extract from *Alipinia speciosa* is selected from the group consisting of a plant extract and a diarylheptanoid;
   c. a *Ricinus communis* (castor) oil, a *Glycyrrhiza glabra* (licorice) root extract, a hydrolyzed oat proteins, a *Citrus medica* limonum (lemon) extract, a *Cucumis sativus* (cucumber) extract, a *Helianthus annus* (sunflower) extract, a carrageenan, a sericin, a butylene glycol, and a xanthan gum; and,
   d. at least one DNA repair enzyme.

2. The method of claim 1 where the at least one DNA repair enzyme is a pyrimidine glycosylate/abasic lyase.

3. The method of claim 2 where the at least one DNA repair enzyme is selected from the group consisting of a bacteriophage T4 pyrimidine dimer-specific endonuclease, a *Micrococcus luteus* N-glycosylase/AP lyase, a *Saccharomyces cerevisiae* N-glycosylase/apurinic-apyrimidinic lyase, a *Schizosaccharomyces pombe* UV damage endonuclease (UVDE), a Chlorella virus isolate PBCV-1 pyrimidine dimer-specific glycosylase, an *Anacystis nidulans* photolyase, and combinations thereof.

4. The method of claim 1 where the composition is in a product form selected from the group consisting of an aerosol, a cream, a emulsion, a solid, a liquid, a dispersion, a foam, a gel, a lotion, a mousse, an ointment, a powder, a patch, a pomade, a solution, a pump a spray, a stick, a towelette, and combinations thereof.

5. The method of claim 1 where the at least one pharmaceutically or cosmetically acceptable vehicle includes one or more ingredients selected from the group consisting of water, a glycerin, a C1-C4 alcohols, a fatty alcohols, a fatty ethers, a fatty esters, a polyols, a glycols, a vegetable oils, a mineral oils, a liposomes, a laminar lipid materials, a silicone oils, and combinations thereof.

6. The method of claim 1 wherein the composition includes at least one pharmaceutically or cosmetically acceptable vehicle.

7. The method of claim 6 wherein the at least one pharmaceutically or cosmetically acceptable vehicle is a liposome.

8. The method of claim 7 wherein the liposome encapsulates the at least one plant ingredient or plant extract from *Rosmarinus officinalis, Centella, Echinacea* or *Alpinia*.

9. The method of claim 7 wherein the liposome encapsulates the at least one DNA repair enzyme.

* * * * *